United States Patent [19]

Taninaka et al.

[11] 4,034,102
[45] July 5, 1977

[54] 4-SUBSTITUTED-1,3-DITHIOLAN-2-YLIDENE MALONATES AND PHARMACEUTICAL COMPOSITIONS CONTAINING THE SAME

[75] Inventors: Kuniaki Taninaka, Ibaragi; Hitoshi Kurono, Amagasaki; Tsutomu Kasai, Sakai, all of Japan

[73] Assignee: Nihon Nohyaku Co. Ltd., Tokyo, Japan

[22] Filed: June 6, 1975

[21] Appl. No.: 584,410

[52] U.S. Cl. .......................... 424/277; 260/327 M
[51] Int. Cl.² .............. A61K 31/385; C07D 339/06
[58] Field of Search ............... 260/327 M; 424/277

[56] References Cited
UNITED STATES PATENTS

| | | | |
|---|---|---|---|
| 3,544,594 | 12/1970 | Grim | 260/327 M |
| 3,761,596 | 9/1973 | Taninaka et al. | 424/277 |
| 3,856,812 | 12/1974 | Taninaka et al. | 424/277 X |

*Primary Examiner*—Frederick E. Waddell
*Attorney, Agent, or Firm*—Karl W. Flocks

[57] ABSTRACT

A 1,3-dithiolan-2-ylidene malonate derivative having the formula,

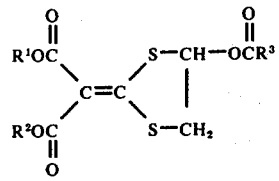

(I)

wherein $R^1$ and $R^2$, which may be same or different, represent individually a $C_1$-$C_4$ alkyl group; and $R^3$ represents a chloromethyl group, a phenyl group, a group of the formula

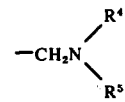

(where $R^4$ and $R^5$ represent individually a $C_1$-$C_4$ alkyl group, or may form, in combination, a lower alkylene group which is sometimes intercepted by an oxygen atom), or a group of the formula

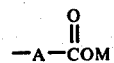

(where M represents a hydrogen atom or a salt-foming residue; and A represents a lower alkylene group, a lower alkenylene group, a phenylene group or a cyclohexenylene group), has effects of stimulating, improving and recovering the functions of livers, and can prevent, alleviate and cure various liver damages of humans and animals when administered thereto either orally or parenterally.

28 Claims, No Drawings

4-SUBSTITUTED-1,3-DITHIOLAN-2-YLIDENE MALONATES AND PHARMACEUTICAL COMPOSITIONS CONTAINING THE SAME

This invention relates to a compound valuable as a medicine for the control of liver damages, and to a pharmaceutical composition containing the same.

The invention further relates to a pharmaceutical composition in the form of administration unit which contains the compound as active ingredient, either alone or in admixture with a pharmaceutically acceptable diluent.

The invention further pertains to a process for controlling the liver damages of humans and animals which comprises administering to the humans or animals a pharmaceutical composition in the form of administration unit which contains the compound as active ingredient, either alone or in admixture with a pharmaceutically acceptable diluent.

The term "controlling the liver damages" or the like, referred to in the body and the claims, means to prevent, alleviate or cure the liver damages.

In view of its various functions, the liver is frequently called a delicate chemical factory. Thus, in the liver, various chemical reactions are being biochemically effected, such as detoxication, sugar metabolism, protein metabolism, lipid metabolism, formation and secretion of bile, control of hormones, formation of blood coagulant prothrombin, regeneration of liver cells, and storage of various living body-constituting elements (fats, glycogens, proteins and vitamins).

However, even such delicate and well-balanced functions of the liver sometime undergo damages, either acutely or chronically, due to various factors such as alcohols, insufficient nutrition, viruses, chemicals, toxicants, etc. to cause such diseases as, for example, hepatitis, jaundice, fatty liver, liver necrosis hepatocirrhosis and liver cancer.

As the result of extensive studies, the present inventors have found that certain 4-substituted-1,3-dithiolan-2-ylidene malonates haveactions to activate liver cells and to activate various metabolic functions of the liver, and hence can improve the damaged liver functions to provide such pharmacological effects as to alleviate or cure the damages and to protect the liver functions from certain damages.

An object of the present invention is to provide a novel compound useful for controlling the liver damages of humans and animals.

Another object of the invention is to provide a novel pharmaceutical composition.

A further object of the invention is to provide a process for controlling the liver damages of humans and animals.

Other objects and advantages of the invention will become apparent from the following description.

In accordance with the present invention, there is provided a compound having the general formula (I),

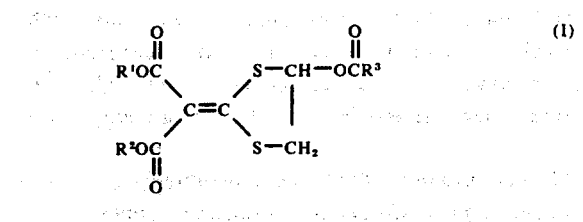

wherein $R^1$ and $R^2$ which may be same or different, represent individually a $C_1-C_4$ alkyl group; and $R^3$ represents a chloromethyl group, a phenyl group, a group of the formula

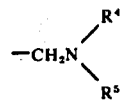

(where $R^4$ and $R^5$ represent individually a $C_1-C_4$ alkyl group, or may form, in combination, a lower alkylene group which is sometimes intercepted by an oxygen atom), or a group of the formula

(where M represents a hydrogen atom or a salt-forming residue; and A represents a lower alkylene group, a lower alkenylene group, a phenylene group or a cyclohexenylene group).

The compounds represented by the aforesaid general formula (I) are novel compounds, and can be synthesized according to the processes described below, using $C_1-C_4$ dialkyl 4-hydroxy-1,3-dithiolan-2-ylidene malonates as starting materials, though the processes vary depending on the kind of the group $R^3$ in the general formula (I).

The processes for synthesizing the compounds of the present invention, including the process for preparing the starting material, are shown below by way of reaction schema.

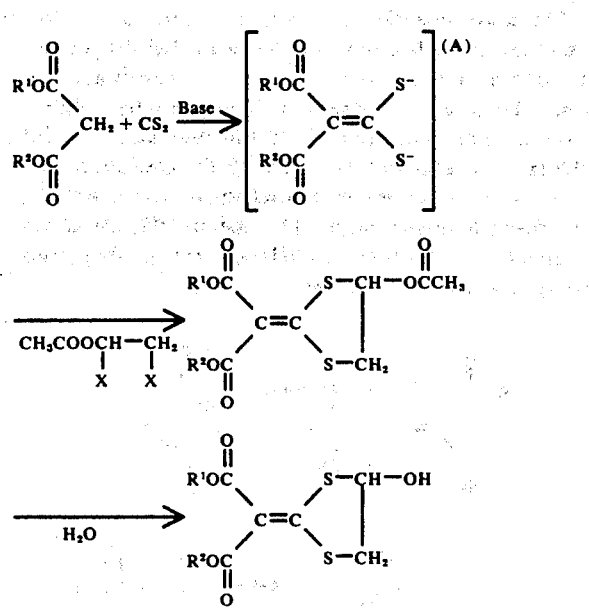

wherein $R^1$ and $R^2$ are as defined previously; and X represents a halogen atom.

This reaction scheme shows a process for preparing dialkyl 4-hydroxy-1,3-dithiolan-2-ylidene malonates which are the starting materials for synthesizing the present compounds. That is, malonic acid esters are reacted with carbon disulfide in the presence of a suitable base, and the resulting dithiolates are reacted with 1-acetoxy-1,2,-dihalogenoethanes to form dialkyl 4-acetoxy-1,3-dithiolan-2-ylidene malonates, which are then hydrolyzed under proper conditions to obtain dialkyl 4-hydroxy-1,3-dithiolan-2-ylidene malonates.

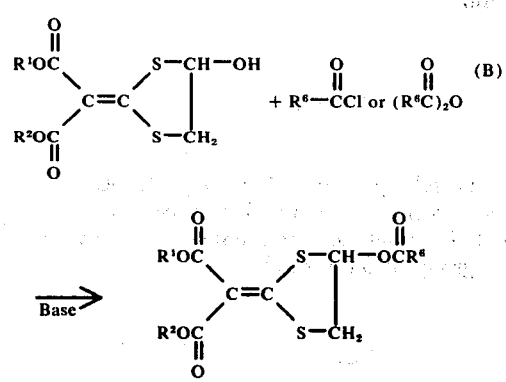

wherein $R^1$ and $R^2$ are as defined previously; and $R^6$ represents a chloromethyl or phenyl group.

This reaction scheme shows a process for synthesizing certain kinds of the present compounds. That is, dialkyl 4-hydroxy-1,3-dithiolan-2-ylidene malonates are reacted with an acid chloride or anhydride in the presence of a suitable base, whereby corresponding end compounds can be obtained. The solvent usable in the above reaction is an anhydrous solvent such as dry ether, dioxane or benzene, or may be water or a hydrous solvent, and the solvent usable in the reaction is an organic base such as pyridine or triethylamine, or an inorganic base such as sodium hydroxide or potassium hydroxide, though these are not limitative.

The above-mentioned reaction is carried out, for example, in such a manner that a dialkyl 4-hydroxy-1,3-dithiolan-2-ylidene malonate is suspended in a solvent, the resulting suspension is incorporated with a base in an amount equimolar to the malonate, an acid chloride or anhydride is gradually dropped into the suspension at room temperature (about 20° to 30° C.), and then the reaction liquid is heated to 50° to 80° C. to complete the reaction, whereby a corresponding end compound can be obtained.

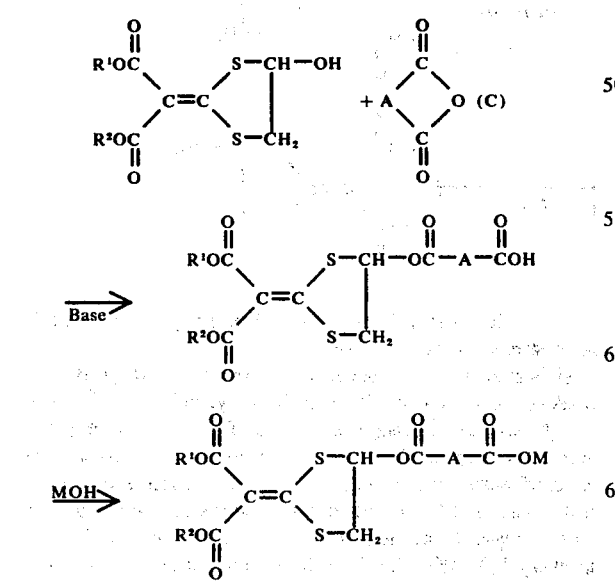

This reaction scheme also shows a process for synthesizing certain kinds of the present compounds. That is, dialkyl 4-hydroxy-1,3-dithiolan-2-ylidene malonates are reacted with an anhydride of a dibasic acid in the presence of a suitable base, whereby corresponding end compounds (semi-esters) can be obtained.

As the base, there may be used any of anhydrous pyridine, triethylamine, etc. Among these, pyridine is preferable since it serves also as a solvent. As the acid anhydride, there is used an anhydride of a dibasic acid such as succinic, glutaric, maleic, phthalic or tetrahydrophthalic acid. The reaction is preferably carried out at or below room temperature, and, even after completion of the reaction, the reaction liquid is desirably not heated. If desired, the resulting semi-esters can be easily converted into pharmaceutically acceptable salts by treatment with an alkali (MOH). Examples of the MOH include sodium hydroxide, potassium hydroxide, ammonia, sodium bicarbonate and potassium bicarbonate.

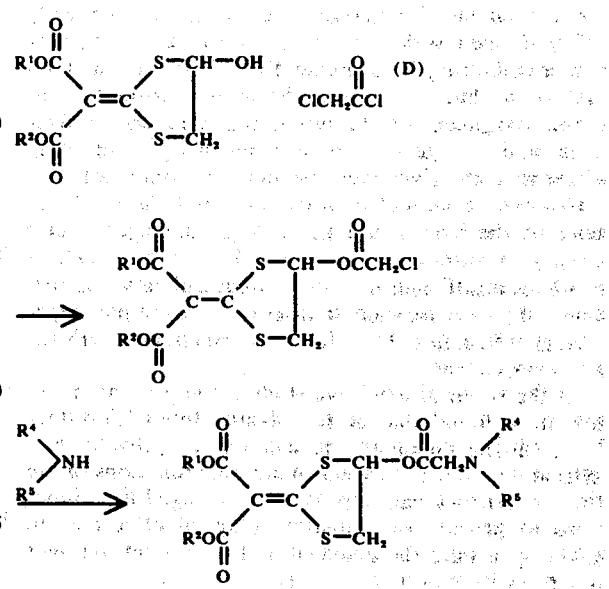

wherein $R^1$, $R^2$, $R^4$, and $R^5$ are as defined previously.

This reaction scheme also shows a process for synthesizing certain kinds of the present compounds. That is, dialkyl 4-monochloroacetoxy-1,3-dithiolan-2ylidene malonates, which are obtained by reacting dialkyl 4-hydroxy-1,3-dithiolan-2-ylidene malonates with a chloride of monochloroacetic acid according to the process shown in the aforesaid (B), are reacted under reflux with two equivalents of a secondary amine or a cyclic amine, whereby corresponding end compounds can be obtained. Preferable as the solvent used in the reaction is a non-polar solvent such as, for example, ether, tetrahydrofuran, dixane or benzene. The reaction temperature is preferably about room temperature to 80° C.

Typical examples of the compounds represented by the general formula (I) are as shown in Table 1.

Table 1

$$\begin{array}{c} R^1OC(=O) \\ \phantom{R^1OC}C=C \\ R^2OC(=O) \end{array} \begin{array}{c} S-CH-OC(=O)R^3 \\ \phantom{S-}| \\ S-CH_2 \end{array} \quad (I)$$

| Compound No. | R¹ | R² | R³ | m.p. (° C) or Refractive index |
|---|---|---|---|---|
| 1 | $C_2H_5$ | $C_2H_5$ | $ClCH_2$ | m.p. 96 – 97° C |
| 2 | $C_2H_5$ | $C_2H_5$ | $HOC(=O)CH_2CH_2$ | m.p. 92 – 93° C |
| 3 | $C_2H_5$ | $C_2H_5$ | $HOC(=O)CH_2CH_2CH_2$ | $n_D^{20}$ 1.5515 |
| 4 | $C_2H_5$ | $C_2H_5$ | $KOC(=O)CH_2CH_2$ | m.p. 71.5 – 74° C |
| 5 | $C_2H_5$ | $C_2H_5$ | $(C_2H_5)_2NCH_2$ | $n_D^{20}$ 1.5453 |
| 6 | $C_2H_5$ | $C_2H_5$ | $(n\text{-}C_3H_7)_2NCH_2$ | $n_D^{20}$ 1.5348 |
| 7 | $C_2H_5$ | $C_2H_5$ | $HOC(=O)$-(2-methylcyclohexenyl) | m.p. 44 – 46° C |
| 8 | $n\text{-}C_3H_7$ | $n\text{-}C_3H_7$ | $HOC(=O)CH_2CH_2$ | $n_D^{20}$ 1.5401 |
| 9 | $i\text{-}C_3H_7$ | $i\text{-}C_3H_7$ | $ClCH_2$ | m.p. 95 – 97° C |
| 10 | $i\text{-}C_3H_7$ | $i\text{-}C_3H_7$ | $C_6H_5$ | m.p. 92 – 93° C |
| 11 | $i\text{-}C_3H_7$ | $i\text{-}C_3H_7$ | $HOC(=O)CH_2CH_2$ | m.p. 125 – 126° C |
| 12 | $i\text{-}C_3H_7$ | $i\text{-}C_3H_7$ | $NaOC(=O)CH_2CH_2$ | |
| 13 | $i\text{-}C_3H_7$ | $i\text{-}C_3H_7$ | $NH_4OC(=O)CH_2CH_2$ | m.p. 78 – 83° C |
| 14 | $i\text{-}C_3H_7$ | $i\text{-}C_3H_7$ | $HOC(=O)CH_2CH_2CH_2$ | $n_D^{20}$ 1.5393 |
| 15 | $i\text{-}C_3H_7$ | $i\text{-}C_3H_7$ | $HOC(=O)CH=CH$ | $n_D^{20}$ 1.5811 |
| 16 | $i\text{-}C_3H_7$ | $i\text{-}C_3H_7$ | $HOC(=O)$-(2-methylphenyl) | m.p. 130 – 131° C |
| 17 | $i\text{-}C_3H_7$ | $i\text{-}C_3H_7$ | $HOC(=O)$-(2-methylcyclohexenyl) | m.p. 104 – 111° C |
| 18 | $i\text{-}C_3H_7$ | $i\text{-}C_3H_7$ | $HOC(=O)$-(cyclohexenyl) | |
| 19 | $i\text{-}C_3H_7$ | $i\text{-}C_3H_7$ | $(C_2H_5)_2NCH_2$ | m.p. 70.5 – 71° C |
| 20 | $i\text{-}C_3H_7$ | $i\text{-}C_3H_7$ | piperidinomethyl | $n_D^{25}$ 1.5451 |
| 21 | $i\text{-}C_3H_7$ | $i\text{-}C_3H_7$ | morpholinomethyl | $n_D^{25}$ 1.5455 |
| 22 | $n\text{-}C_4H_9$ | $n\text{-}C_4H_9$ | morpholinomethyl | $n_D^{25}$ 1.5449 |

Table 1-continued $$\begin{array}{c} R^1OC \\ \parallel \\ O \end{array} \diagdown C=C \diagup \begin{array}{c} S-CH-OCR^3 \\ \parallel \\ O \end{array} \qquad (I)$$
$$R^2OC \diagup \qquad \diagdown S-CH_2 \\ \parallel \\ O$$

| Compound No. | R¹ | R² | R³ | m.p. (° C) or Refractive index |
|---|---|---|---|---|
| 23 | $C_2H_5$ | $C_2H_5$ | $O\diagdown\begin{array}{c}CH_2-CH_2\\CH_2-CH_2\end{array}\diagup N-CH_2-$ | $n_D^{25}$ 1.5646 |

The compounds represented by the general formula (I) are extremely low in toxicity to mammals, and their acute oral toxicity to male mice expressed as $LD_{50}$ values are at such a low toxicity level as in the range from 1,000 to 6,000 mg/kg or more, in general. For example, the $LD_{50}$ value of the compound 12 is more than 3,000 mg/kg. Further, these compounds have no detrimental effects on test animals administered therewith, so far as the doses thereof are within an ordinary administration range.

The compounds of the general formula (I) ar usable as pharmaceuticals for humans and animals. They have broad and vairous pharmaceutical spectra. The compound of the formula (I) has effects of stimulating, improving and recovering the functions of livers, and can prevent, alleviate and cure vairous liver damages of humans and animals when administered thereto either orally or parenterally. The compounds may also be administered in the form of suppositories. Concretely, they can show in animal tests such main effects as described below.

1. They have effects of preventing, alleviating and curing liver damages (e.g. necrosis, hepatitis, fatty liver) derived from carbon tetrachloride, chloroform, bromobenzene, dimethyl-nitrosoamine, etc.
2. Accordingly, they are effective for the preventin, alleviation and therapy of liver damages and acute hepatitis due to chemical poisoning.
3. They can prevent, alleviate and cure liver damages derived from administration of ehtionine, and hence are effective for prevention, alleviation and therapy of fatty liver diseases.
4. They have actions to stimulate the alcohol metabolic function of the liver to lower the concentration of alcohol in the blood, and hence are effective for promotion of recovery from alcoholic intoxication and for prevention, alleviatation and therapy of crapulence.
5. They have actions to stimulate the sugar metabolic function of the liver to lower the abnormally elevated concentration of sugar in the blood, and hence are effective as blood sugar depressants and curatives for diabetes.
6. When cadmium or selenium salts are administered to animals, which have previously been administered with the said compounds, the toxic symptoms caused by said salts are far more alleviated than in the case of blank animals.

Accordingly, the compounds represented by the general formula (I) are effective as preventives, alleviatives and curatives for liver damages, acute hepatitis, fatty liver diseases and chemical poisoning. Further, the said compounds are effective as depressants of alcohol in the blood, blood sugar depressants, diabetes curatives, and drugs for stimulating, promoting, improving and recovering metabolic functions of the livers.

In using the said compounds as the above-mentioned drugs, they may be formulated, according to usual procedures and means adopted in this field, into pharmaceutical compositions in the form of administration units convenient for their individual application purposes. That is, the said compounds are formulated into pharmaceutical compositions, either along or in admixture with a pharmaceutically acceptable diluent, which may be any one of solids, semi-solids, liquids and intakable capsules, and are administered to humans or animals, either orally or parenterally.

Thus, the present invention provides a pharmaceutical composition which comprises the above-mentioned compound as active ingredient and, in admixture therewith, a pharmaceutically acceptable solid, semi-solid or liquid diluent.

The present invention further provides a pharmaceutical composition containing as active ingredient the above-mentioned compound in the form of a sterile and/or isotonic aqueous solution.

The present invention still further provides a pharmaceutical composition in the form of administration unit which contains the above-mentioned compound either along or in admixture with a pharmaceutically acceptable diluent.

The pharmaceutical composition of the present invention can be provided in such various administration unit forms as powders, granules, tablets, sugar-coated tablets, pills, capsules, suppositories, suspensions, liquids, emulsions, ampoules and injections.

The present invention includes such mode that the above-mentioned compound as active ingredient is administered singly. The present invention further includes such mode that the above-mentioned compound is administered in the form of a mixture with a pharmacuetically acceptable diluent. The diluent referred to herein means not only a mere diluent but also a pharmaceutically acceptable usual adjuvant. Examples of the mere diluent are those which are ordinarily used in the pharmaceutical field, and include such solid diluents as starch, lactose, calcium hydrogen phosphate, heavy magnesium oxide and the like, and such liquid diluents as water, isotonic solution, glucose solution and the like. Examples of the adjuvant include vehicles, extenders, binders, wetting agents, disintegrators, surfactants, lubricants, dispersants, buffer agents, seasonings, deodorants, dyes, flavors, preservatives and dissolution aids, though these are not limitative. These adjuvants may be used either singly or in the form of a mixture of two or more members.

The pharmaceutical composition of the present invention may be prepared according to any known method. For example, a mixture of the active ingredient and a diluent is formed, for example, into granules, and the the thus formed granular composition is molded, for example, into tablets. In case the pharmaceutical composition is for parenteral administration, it is preferable to be made aseptic and, if necessary, be made isotonic to the blood.

Generally, the pharmaceutical composition of the present invention contains about 0.01 to 100% by weight, based on the weight of the composition, of the active compound. Thus, the present invention includes such mode that the said compound is used independently.

The pharmaceutical composition of the present invention may be incorporated with other pharmaceutically active compound. In some cases, the composition may be incorporated with a plurality of the present compounds.

For the control of various liver damages and various diseases derived therefrom, the pharmaceutical composition of the present invention may be applied according to an ordinary procedure adopted in this field, in order to attain such effects as shown in the aforesaid animal tests. Thus, the composition of the present invention is administered orally or parenterally. The oral administration includes sublingual administration, and the parenteral administration includes administration by way of injection including, for example, subcutaneous, intramuscular and intravenous injection.

Effective does of the present compound is advantageously in the range from 0.1 to 500 mg. per kg. body weight per day in the case of oral administration, and in the range from 0.01 to 250 mg. kg. body weight per day in the case of parenteral administration. However, the above-mentioned ranges vary depending on the body weight and physical condition of test animal, the manner of administration, the kind and properties of pharmaceutical composition, the time and interval of administration, the kind of disease, etc. Accordingly, in some cases, the dose of the present compound may be made smaller than the minimum dose mentioned above, while in other cases, the dose of the present compound would be in excess of the maximum dose mentioned above. In case the present compound is to be administered in a large dose, it is preferably that the compound is divisionally administered several times a day.

The present invention is illustrated in more detail below with reference to examples, but the invention is not limited to the examples.

EXAMPLE 1

Synthesis of diisoproyl 4-benzyloxy-1,3-dithiolan-2-ylidene malonate (Compound 10 in Table 1)

30.5 Grams (0.1 mole) of a diisopropyl ester of 4-hydroxy-1,3-dithiolan-2-ylidene malonic acid and 10 g (0.1 mole) of triethylamine were dissolved in 150 ml of dioxane. Into the resulting solution, 14 g (0.1 mole) of benzoyl chloride was dropped at 30° to 40° C. The resulting mixture was reacted at said temperature for 1 hour and then at 60°-80° C for 2 hours. After completion of the reaction, the formed triethylamine hydrochloride was removed by filtration, and then the dioxane was removed by distillation. Subsequently, the residue was recrystallized from an ether-n-hexane mixed solvent to obtain 34 g of white crystals, m.p. 92°–93° C, yield 85%.

EXAMPLE 2

Synthesis of diisopropyl 4-chloroacetoxy-1,3-dithiolan-2-ylidene malonate (Compound 9 in Table 1)

15.2 Grams (0.05 mole) of a diisopropyl ester of 4-hydroxy-1,3-dithiolan-2-ylidene malonic acid and 5 g (0.05 mole) of triethylamine were dissolved in 200 ml of benzene. Into the resulting solution, 5.7 g (0.1 mole) of chloroacetyl chloride was dropped at room temperature. The resulting mixture was reacted at said temperature for 2 hours and then at 60° to 70° C for 2 hours. After cooling the reaction liquid, the formed triethylamine hydrochloride was removed by filtration, and then the benzene was removed by distillation. Subsequently, the residue was recrystallized from ether to obtain 27.5 g of white crystals, m.p. 95°–97° C, yield 72.5%.

EXAMPLE 3

Synthesis of phthalic acid semi-ester of diisopropyl 4-hydroxy-1,3-dithiolan-2-ylidene malonate (Compound 16 in Table 1)

15.2 Grams (0.05 mole) of a diisopropyl ester of 4-hydroxy-1,3-dithiolan-2-ylidene malonic acid and 7.4 g (0.05 mole) of a phthalic anhydride were dissolved in 250 ml of pyridine. The resulting solution was allowed to stand at room temperature for 24 hours, and then the pyridine was removed by distillation under reduced pressure at about 50° C to obtain an oily substance. This oily substance was washed with dilute hydrochloric acid and water, whereby pale yellow crude crystals were obtained. Subsequently, the crude crystals were recrystallized from ether to obtain 18.5 g of crystals, m.p. 130°–131° C, yield 82.2%.

EXAMPLE 4

Synthesis of succinic acid semi-ester of diisopropyl 4-hydroxy-1,3-dithiolan-2-ylidene malonate (Compound 11)

61.2 Grams (0.2 mole) of a diisopropyl ester of 4-hydroxy-1,3-dithiolan-2-ylidene malonic acid and 22 g (0.2 mole) of a succinic anhydride were dissolved in 200 ml of pyridine. The resulting solution was allowed to stand at room temperature for 24 hours, and then the pyridine was removed by distillation under reduced pressure at below 50° C to obtain an oily substance. This oily substance was poured into dilute hydrochloric acid to deposit crystals. The deposited crystals were recovered by filtration, washed with water, dried, and then recrystallized from ethyl acetate to obtain 60 g of white crystals, m.p. 125°–126° C, yield 72%.

Synthesis of ammonium salt of the above mentioned semi-ester

2 Grams of the semi-ester was dissolved in 20 ml of ether. Into the resulting solution, a dry ammonia gas was introduced to deposit crystals. The deposited crystals were recovered by filtration to obtain white crystals in a quantitative yield, m.p. 78°–83° C.

Synthesis of sodium salt of the above-mentioned semi-ester

2 Grams of the semi-ester was dissolved in 15 ml of a 30% aqeous sodium bicarbonate solution. The resulting solution was subjected to freeze-drying, and then charged with 10 ml of chloroform to deposit crstals. The depoited crystals were recovered by filtration and then dissolved in water. The resulting solution was subjected two times to the same operation as above to obtain crystals of the desired product, m.p. 89°–90° C.

EXAMPLE 5

Synthesis of diisopropyl 4-diethylaminoacetoxy-1,3-dithiolan-2-ylidene malonate (Compound 19)

3.8 Grams (0.01 mole) of the dissopropyl ester of 4-chloroacetoxy-1,3-dithiolan-2-ylidene malonic acid obtained in Example 2 was dissolved in 50 ml of tetrahydrofuran. To the resulting solution was added 1.5 g (0.02 mole) of dithylamine, and the resulting mixture was refluxed for 3 hours. After the reaction, the formed diethylamine hydrochloride was removed by filtration, and then the tetrahydrofuran was removed by distillation. The residue was washed with water and then extracted with IN—HC1. The extract was neutralized with a dilute aqueous sodium hydroxide solution to form an oily substance. This oily substance was extracted with ether, and the ether extract was washed with water, dried and the freed from the ether by distillation, whereby 3.5 g of crude crystals of the desired product were obtained Subsequently, the crude crystals were recrystallized from n-hexane to obtain 3.1 g of white crystals, m.p. 70.5°–71° C, yield 74%.

In Examples 6 to 13 described below, all parts are by weight.

EXAMPLE 6

| | |
|---|---|
| Succinic acid semi-ester of diethyl 4-hydroxy-1,3-dithiolan-2-ylidene malonate (Compound 2) | 10 parts |
| Heavy magnesium oxide | 10 parts |
| Lactose | 80 parts |

The above-mentioned components were homogeneously mixed and pulverized to obtain a powder.

EXAMPLE 7

| | |
|---|---|
| Succinic acid semi-ester of diisopropyl 4-hydroxy-1,3-dithiolan-2-ylidene malonate (Compound 11) | 10 parts |
| Synthetic aluminum silicate | 10 parts |
| Calcium hydrogenphosphate | 5 parts |
| Lactose | 75 parts |

The above-mentioned components were treated in the same manner as in Example 6 to obtain a powder.

EXAMPLE 8

| | |
|---|---|
| Diethyl 4-diethylaminoacetoxy-1,3-dithiolan-2-ylidene malonate (Compound 5) | 50 parts |
| Starch | 10 parts |
| Lactose | 15 parts |
| Crystalline cellulose | 20 parts |
| Polyvinyl alcohol | 5 parts |

-continued

| | |
|---|---|
| Water | 30 parts |

The above-mentioned components were homogeneously kneaded, granulated, dried and sieved to obtain a granule.

EXAMPLE 9

99 Parts of the granule obtained in Example 8 was incorporated with 1 part of calcium stearate, and then subjected to compression molding to obtain a tablet of 10 mm in diameter.

EXAMPLE 10

| | |
|---|---|
| Phthalic acid semi-ester of diisopropyl 4-hydroxy-1,3-dithiolan-2-ylidene malonate (Compound 16) | 95 parts |
| Polyvinyl alcohol | 5 parts |
| Water | 30 parts |

The above-mentioned components were treated in the same manner as in Example 8 to obtain a granule. 90 Parts of the thus obtained granule was incorporated with 10 parts of crystalline cellulose, and then subjected to compression molding to obtain a tablet of 8 mm in diameter. Further, this tablet was formed into a sugar-coated tablet by use of proper amounts of a suspension comprising ethanolic shellac, syrup gelatin and precipitated calcium carbonate, and a dye.

EXAMPLE 11

| | |
|---|---|
| Diisopropyl 4-diethylaminoacetoxy-1,3-dithiolan-2-ylidene malonate (Compound 19) | 4 parts |
| Nonionic surfactant | 10 parts |
| Isotonic sodium chloride solution | 86 parts |

The above-mentioned components were mixed together with heating to form a solution, which was then cooled to obtain an injection.

EXAMPLE 12

| | |
|---|---|
| Succinic acid semi-ester of di-n-propyl 4-hydroxy-1,3-dithiolan-2-ylidene malonate (Compound 8) | 0.5 part |
| Nonionic surfactant | 2.5 part |
| Distilled water for injection | 97.0 part |

The above-mentioned components were treated in the same manner as in Example 11 to obtain an injection.

EXAMPLE 13

The powder obtained in Example 6 was filled into commercially available capsules to prepare a capsule.

EXAMPLE 14

Protection against CCl$_4$-induced Hepatotoxicity

Carbon tetrachloride (CCl$_4$) administration induces centrilobular necrosis of the liver associated with loss of diphosphopyridine nucleotide, hepatic glycogen, coenzyme A and increase in neutral fat. Release of several enzymes from the hepatocytes, and increase of enzyme activities in the plasma are recognized as the result of the damage of the liver. A suitable means for evaluating the degree of damage induced by CCl₄ or the degree of protection afforded by drugs is to study the plasma glutamic-pyruvic transaminase (p-GPT) activity.

Methods: The test compounds were dissolved or suspended in olive oil and administered orally at the dose of 250 mg/kg to the mice (Four-week-old male mice-dd strain). After 6 hours, CCl₄ was administered orally (0.05 ml/kg as olive oil solution). Animals were killed 24 hours after CCl₄ administration, and the liver was grossly observed. The plasma was obtained by centrifugation. Activities of p-GPT were determined by the method of Reitman and Frankels and expressed in Karmen units. Score for liver damage index was as follows:

| Liver damage index | Description |
| --- | --- |
| 0 | Normal |
| 2 | Slightly recognized |
| 4 | Clearly observable damage |
| 6 | Heavy damage |

Each figure indicates average of 5 to 6 mice. Values of p-GPT over 1,000 Karmer unit regarded as 1,000 for calculation of average for convenience.

Table 2

| Results: Compound No. | Liver damage index | p-GPT |
| --- | --- | --- |
| 1 | 1.0 | 102 |
| 2 | 0.6 | 43 |
| 3 | 1.2 | 108 |
| 4 | 0.2 | 45 |
| 5 | 1.6 | 232 |
| 6 | 1.6 | 250 |
| 7 | 2.2 | 382 |
| 8 | 0.6 | 77 |
| 9 | 0.6 | 65 |
| 10 | 1.7 | 520 |
| 11 | 0.2 | 54 |
| 12 | 0.2 | 33 |
| 13 | 0.6 | 44 |
| 14 | 0.6 | 102 |
| 15 | 0.4 | 62 |
| 16 | 3.2 | 482 |
| 17 | 1.8 | 286 |
| 18 | 2.6 | 565 |
| 19 | 1.2 | 288 |
| 20 | 1.4 | 242 |
| 21 | 1.4 | 380 |
| 22 | 0.8 | 134 |
| 23 | 0.8 | 122 |
| CCl₄ alone | 5.2 | >1000 |
| Thioctic acid amide | 4.8 | 763 |
| Anethol trithion | 1.6 | 58 |
| Control | 0 | 35 |

Carbon tetrachloride is best suitable for bringing test animals to the state of acute hepatitis. As is clear from the results of tests carried out by use of carbon tetrachloride, all the active ingredients used in the present composition show prominent liver damage-preventing effects, and are comparable in effectiveness to thioctic acid amide and anethol trithion which are commercially available at present as liver drugs.

What is claimed is:
1. A compound represented by the general formula

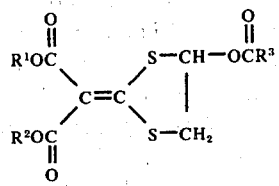

wherein $R^1$ and $R^2$, which may be same or different, represent individually a $C_1$–$C_4$ alkyl group; and $R^3$ represents a chloromethyl group, a phenyl group, a group of the formula

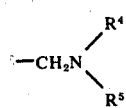

(where $R^4$ and $R^5$ represent individually a $C_1$–$C_4$ alkyl group, or a group of the formula

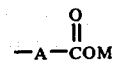

(where M represents a hydrogen atom or a pharmaceutically acceptable salt-forming residue; and A represents a lower alkylene group, a lower alkenylene group, a phenylene group or a cyclohexenylene group).

2. A succinic acid semi-ester of diisopropyl 4-hydroxy-1,3-dithiolan-2-ylidene malonate, or a pharmaceutically acceptable salt thereof.

3. A succinic acid semi-ester of diethyl 4-hydroxy-1,3-dithiolan-2-ylidene malonate, or a pharmaceutically acceptable salt thereof.

4. Diisopropyl 4-diethylaminoacetoxy-1,3-dithiolan-2-ylidene malonate.

5. Diethyl 4-dithylaminoacetoxy-1,3-dithiolan-2-ylidene malonate.

6. A pharmaceutical composition for preventing liver necrosis, fatty liver or hepatitis of animals including humans, which comprises an effective amount sufficient for said purpose of a compound having the general formula (I) defined in claim 1, and a pharmaceutically acceptable diluent.

7. The composition of claim 6 which contains the said compound in an amount of at least 0.01% by weight.

8. The composition of claim 6, wherein the compound is a succinic acid semi-ester of diisopropyl 4-hydroxyl-1,3-dithiolan-2-ylidene malonate, or a pharmaceutically acceptable salt thereof.

9. The compositon of claim 6, wherein the compound is a succinic acid semi-ester of diethyl 4-hydroxy-1,3-dithiolan-2-ylidene malonate, or a pharmaceutically acceptable salt thereof.

10. The composition of claim 6, wherein the compoundd is diisopropyl 4-diethylamonoacetoxy-1,3-dithiolan-2-ylidene malonate.

11. The composition of claim 6, wherein the compound is diethyl 4-diethylaminoacetoxy-1,3-dithiolan-2-ylidene malonate.

12. The composition of claim 6, wherein the compound is formulated into an administration unit form.

13. The composition of claim 12, wherein the administration unit form is any one of powder, granule, tablet, pill, sugar-coated tablet, capsule, ampoule, suppository, suspension, liquid, emulsion or injection.

14. The composition of claim 12, wherein the compound is a succinic acid semi-ester of diisopropyl 4-hydroxy-1,3-dithiolan-2-ylidene malonate, or a pharmaceutically acceptable salt thereof.

15. The composition of claim 12, wherein the compound is a succinic acid semi-ester of diethyl 4-hydroxy-1,3-dithiolan-2-ylidene malonate, or a pharmaceutically acceptable salt thereof.

16. The composition of claim 12, wherein the compound is diisopropyl 4-diethylaminoacetoxy-1,3-dithiolan-2-ylidene malonate.

17. The composition of claim 12, wherein the compound is diethyl 4diethylaminoacetoxy-1,3-dithiolan-2-ylidene malonate.

18. A process for preventing liver necrosis, fatty liver or hepatitis of animals including humans which comprises administering orally or parenterally, to the animals an effective does sufficient for said purposes of a compound having the general formula (I) defined in claim 1.

19. The process of claim 18, wherein the compound is administered parenterally.

20. The process of claim 19, wherein the dose of the compound is in the range from 0.01 to 250 mg per kg body weight per day.

21. The process of claim 18, wherein the compound is administered orally.

22. The process of claim 21, wherein the dose of the compound is in the range from 0.1 to 500 mg per kg body weight per day.

23. The proces of claim 18, wherein the compound is a succinic acid semi-ester of diisopropyl 4-hydroxy-1,3-dithiolan-2-ylidene malonate, or a pharmaceutically acceptable salt thereof.

24. The process of claim 18, wherein the compound is a succinic acid semi-ester of diethyl 4-hydroxy-1,3-dithiolan-2-ylidene malonate or a pharmaceutically acceptable salt thereof.

25. The process of claim 18, wherein compound is diisopropyl 4-diethylaminoacetoxy-1,3-dithiolan-2-ylidene malonate.

26. The process of claim 18, wherein the compound is diethyl 4-diethylaminoacetoxy-1,3-dithiolan-2-ylidene malonate.

27. The process of claim 18, wherein said necrosis, fatty liver or hepatitis is induced by chemical poisoning.

28. The process of claim 27, wherein the chemical causing said poisoning is carbontetrachloride, chloroform, bromobenezene, dimethyl-nitrosoamine, ethionine, a cadmium salt or a selenium salt.

* * * * *